United States Patent
Bitton et al.

(10) Patent No.: US 8,295,932 B2
(45) Date of Patent: Oct. 23, 2012

(54) INGESTIBLE CAPSULE FOR APPETITE REGULATION

(75) Inventors: Ophir Bitton, Zichron Yaakov (IL); Shai Policker, Tenafly, NJ (US); Benny Rousso, Rishon LeZion (IL)

(73) Assignee: Metacure Limited, Hamilton (BM)

( * ) Notice: Subject to any disclaimer, the term of this patent is extended or adjusted under 35 U.S.C. 154(b) by 1113 days.

(21) Appl. No.: 11/566,775

(22) Filed: Dec. 5, 2006

(65) Prior Publication Data

US 2008/0065168 A1   Mar. 13, 2008

Related U.S. Application Data

(60) Provisional application No. 60/742,365, filed on Dec. 5, 2005.

(51) Int. Cl.
*A61N 1/18* (2006.01)
(52) U.S. Cl. .......................................................... 607/40
(58) Field of Classification Search ................ 607/2, 40, 607/72
See application file for complete search history.

(56) References Cited

U.S. PATENT DOCUMENTS

| | | | |
|---|---|---|---|
| 3,411,507 A | 11/1968 | Wingrove | |
| 3,516,412 A | 6/1970 | Ackerman | |
| 3,737,579 A | 6/1973 | Bolduc | |
| 4,000,745 A | 1/1977 | Goldberg et al. | |
| 4,010,758 A | 3/1977 | Rockland et al. | |
| 4,133,315 A | 1/1979 | Berman et al. | |
| 4,177,818 A | 12/1979 | De Pedro | |
| 4,235,246 A | 11/1980 | Weiss | |
| 4,280,503 A | 7/1981 | Ackerman | |
| 4,313,448 A | 2/1982 | Stokes | |
| 4,357,946 A | 11/1982 | Dutcher et al. | |
| 4,378,023 A | 3/1983 | Trabucco | |
| 4,416,267 A | 11/1983 | Garren et al. | |
| 4,452,254 A | 6/1984 | Goldberg et al. | |
| 4,485,805 A | 12/1984 | Foster, Jr. | |
| 4,592,339 A | 6/1986 | Kuzmak | |
| 4,823,808 A | 4/1989 | Clegg et al. | |

(Continued)

FOREIGN PATENT DOCUMENTS

EP   0057048   8/1982

(Continued)

OTHER PUBLICATIONS

Jaremko, et al., "Advances toward the implantable artificial pancreas for treatment of diabetes", Diabetes Care, 21(3), Mar. 1998.

(Continued)

*Primary Examiner* — Niketa Patel
*Assistant Examiner* — Michael D Abreu
(74) *Attorney, Agent, or Firm* — William H. Dippert; Eckert Seamans Cherin & Mellott, LLC (57) ABSTRACT

A method is provided for treating a subject. The method includes administering to the subject an ingestible capsule containing one or more flexible support elements adapted to expand while in a stomach of the subject, thereby bringing a plurality of electrodes into contact with a wall of the stomach. The method also includes driving the electrodes to apply an electrical signal to the stomach wall at first and second times, the second time at last 24 hours after the first time. Other embodiments are also described.

26 Claims, 6 Drawing Sheets

U.S. PATENT DOCUMENTS

| | | | |
|---|---|---|---|
| 4,975,682 A | 12/1990 | Kerr et al. |
| 5,074,868 A | 12/1991 | Kuzmak |
| 5,101,814 A | 4/1992 | Palti |
| 5,103,804 A | 4/1992 | Abele et al. |
| 5,105,812 A | 4/1992 | Corman |
| 5,188,104 A | 2/1993 | Wernicke et al. |
| 5,190,041 A | 3/1993 | Palti |
| 5,226,429 A | 7/1993 | Kuzmak |
| 5,231,988 A | 8/1993 | Wernicke et al. |
| 5,234,454 A | 8/1993 | Bangs |
| 5,247,938 A | 9/1993 | Silverstein et al. |
| 5,263,480 A | 11/1993 | Wernicke et al. |
| 5,314,463 A | 5/1994 | Camps et al. |
| 5,368,028 A | 11/1994 | Palti |
| 5,423,872 A | 6/1995 | Cigaina |
| 5,449,368 A | 9/1995 | Kuzmak |
| 5,514,175 A | 5/1996 | Kim et al. |
| 5,540,730 A | 7/1996 | Terry et al. |
| 5,551,425 A | 9/1996 | Essen-Moller |
| 5,601,604 A | 2/1997 | Vincent |
| 5,690,691 A | 11/1997 | Chen et al. |
| 5,704,368 A | 1/1998 | Asano et al. |
| 5,716,385 A | 2/1998 | Mittal et al. |
| 5,741,211 A | 4/1998 | Renirie et al. |
| 5,792,210 A | 8/1998 | Wamubu et al. |
| 5,795,304 A | 8/1998 | Sun et al. |
| 5,833,625 A | 11/1998 | Essen-Moller |
| 5,836,994 A | 11/1998 | Bourgeois |
| 5,837,006 A | 11/1998 | Ocel et al. |
| 5,861,014 A | 1/1999 | Familoni |
| 5,868,141 A | 2/1999 | Ellias |
| 5,919,216 A * | 7/1999 | Houben et al. .................. 607/72 |
| 5,938,669 A | 8/1999 | Klaiber et al. |
| 5,979,449 A | 11/1999 | Steer |
| 5,991,649 A | 11/1999 | Garfield et al. |
| 5,995,872 A | 11/1999 | Bourgeois |
| 6,026,326 A | 2/2000 | Bardy |
| 6,041,258 A | 3/2000 | Cigaina et al. |
| 6,067,991 A | 5/2000 | Forsell |
| 6,083,249 A | 7/2000 | Familoni |
| 6,091,992 A | 7/2000 | Bourgeois |
| 6,092,528 A | 7/2000 | Edwards |
| 6,093,167 A | 7/2000 | Houben et al. |
| 6,097,984 A | 8/2000 | Douglas |
| 6,104,955 A | 8/2000 | Bourgeois |
| 6,115,635 A | 9/2000 | Bourgeois |
| 6,129,685 A | 10/2000 | Howard |
| 6,132,372 A | 10/2000 | Essen-Moller |
| 6,135,978 A | 10/2000 | Houben |
| 6,216,045 B1 | 4/2001 | Black et al. |
| 6,243,607 B1 | 6/2001 | Mintchev |
| 6,249,697 B1 | 6/2001 | Asano et al. |
| 6,261,280 B1 | 7/2001 | Houben et al. |
| 6,285,897 B1 | 9/2001 | Kilcoyne et al. |
| 6,334,073 B1 | 12/2001 | Levine |
| 6,363,937 B1 | 4/2002 | Hovda et al. |
| 6,381,495 B1 | 4/2002 | Jenkins |
| 6,405,732 B1 | 6/2002 | Edwards |
| 6,411,842 B1 | 6/2002 | Cigaina et al. |
| 6,415,178 B1 | 7/2002 | Ben-Haim et al. |
| 6,427,089 B1 | 7/2002 | Knowlton |
| 6,449,511 B1 | 9/2002 | Mintchev |
| 6,454,699 B1 | 9/2002 | Forsell |
| 6,535,764 B2 | 3/2003 | Imran et al. |
| 6,571,127 B1 | 5/2003 | Ben-Iiaim et al. |
| 6,572,542 B1 | 6/2003 | Houben et al. |
| 6,584,348 B2 | 6/2003 | Glukhovsky |
| 6,591,137 B1 | 7/2003 | Fischell et al. |
| 6,600,953 B2 | 7/2003 | Flesler et al. |
| 6,606,523 B1 | 8/2003 | Jenkins |
| 6,609,025 B2 | 8/2003 | Barrett et al. |
| 6,612,983 B1 | 9/2003 | Marchal |
| 6,652,444 B1 | 11/2003 | Ross |
| 6,658,297 B2 | 12/2003 | Loeb |
| 6,678,561 B2 | 1/2004 | Forsell |
| 6,684,104 B2 | 1/2004 | Gordon |
| 6,709,388 B1 | 3/2004 | Mosse et al. |
| 6,735,477 B2 | 5/2004 | Levine |
| 6,745,079 B2 | 6/2004 | King |
| 6,754,536 B2 | 6/2004 | Swoyer et al. |
| 6,826,428 B1 | 11/2004 | Chen et al. |
| 6,832,114 B1 | 12/2004 | Whitehurst |
| 6,852,110 B2 | 2/2005 | Roy et al. |
| 6,853,862 B1 | 2/2005 | Marchal et al. |
| 6,869,431 B2 | 3/2005 | Maguire et al. |
| 6,876,885 B2 | 4/2005 | Swoyer et al. |
| 6,895,279 B2 | 5/2005 | Loeb et al. |
| 6,918,906 B2 | 7/2005 | Long |
| 6,939,349 B2 | 9/2005 | Fleischman et al. |
| 6,947,792 B2 | 9/2005 | Ben-Haim et al. |
| 6,952,613 B2 | 10/2005 | Swoyer et al. |
| 7,006,871 B1 | 2/2006 | Darvish et al. |
| 7,043,295 B2 | 5/2006 | Starkebaum |
| 7,054,690 B2 | 5/2006 | Imran |
| 7,076,305 B2 | 7/2006 | Imran et al. |
| 7,076,306 B2 | 7/2006 | Marchal et al. |
| 2001/0011543 A1 | 8/2001 | Forsell |
| 2002/0026141 A1 | 2/2002 | Houben |
| 2002/0103424 A1 | 8/2002 | Swoyer et al. |
| 2002/0161414 A1 | 10/2002 | Flesler et al. |
| 2003/0045919 A1 | 3/2003 | Swoyer et al. |
| 2003/0055464 A1 | 3/2003 | Darvish et al. |
| 2003/0055467 A1 | 3/2003 | Ben-Haim et al. |
| 2003/0066536 A1 | 4/2003 | Forsell |
| 2003/0144708 A1 | 7/2003 | Starkebaum |
| 2003/0195600 A1 | 10/2003 | Tronnes et al. |
| 2003/0208212 A1 | 11/2003 | Cigaina |
| 2003/0208242 A1 | 11/2003 | Harel et al. |
| 2003/0220678 A1 | 11/2003 | Tronnes et al. |
| 2004/0044376 A1 | 3/2004 | Flesler et al. |
| 2004/0059393 A1* | 3/2004 | Policker et al. ................. 607/40 |
| 2004/0088023 A1 | 5/2004 | Imran et al. |
| 2004/0107004 A1 | 6/2004 | Levine et al. |
| 2004/0147816 A1 | 7/2004 | Policker et al. |
| 2004/0158138 A1 | 8/2004 | Kilcoyne et al. |
| 2004/0162469 A1 | 8/2004 | Imran |
| 2004/0162595 A1 | 8/2004 | Foley |
| 2004/0167583 A1 | 8/2004 | Knudson et al. |
| 2004/0193184 A1 | 9/2004 | Laufer et al. |
| 2004/0193229 A1 | 9/2004 | Starkebaum et al. |
| 2004/0236316 A1 | 11/2004 | Danitz et al. |
| 2004/0249421 A1* | 12/2004 | Harel et al. ..................... 607/40 |
| 2005/0021101 A1 | 1/2005 | Chen et al. |
| 2005/0055038 A1 | 3/2005 | Kelleher et al. |
| 2005/0065505 A1 | 3/2005 | Ryan |
| 2005/0075654 A1 | 4/2005 | Kelleher |
| 2005/0090873 A1 | 4/2005 | Imran |
| 2005/0107829 A1 | 5/2005 | Edwards et al. |
| 2005/0143784 A1 | 6/2005 | Imran |
| 2005/0164925 A1 | 7/2005 | Jakubowski et al. |
| 2005/0183732 A1 | 8/2005 | Edwards |
| 2005/0192615 A1 | 9/2005 | Torre et al. |
| 2005/0203500 A1 | 9/2005 | Saadat et al. |
| 2005/0209653 A1 | 9/2005 | Herbert et al. |
| 2005/0222638 A1 | 10/2005 | Foley et al. |
| 2006/0074459 A1 | 4/2006 | Flesler et al. |
| 2006/0085045 A1 | 4/2006 | Harel et al. |
| 2006/0142803 A1 | 6/2006 | Mintchev |
| 2006/0173238 A1 | 8/2006 | Starkebaum |
| 2006/0184207 A1 | 8/2006 | Darvish et al. |
| 2006/0247718 A1 | 11/2006 | Starkebaum |
| 2007/0027493 A1 | 2/2007 | Ben-Haim et al. |
| 2007/0051849 A1 | 3/2007 | Watts et al. |
| 2007/0060812 A1 | 3/2007 | Harel et al. |
| 2007/0060971 A1 | 3/2007 | Glasberg et al. |
| 2007/0092446 A1 | 4/2007 | Haddad et al. |
| 2007/0156177 A1 | 7/2007 | Harel et al. |
| 2007/0161851 A1* | 7/2007 | Takizawa et al. ............. 600/102 |
| 2007/0179556 A1 | 8/2007 | Ben Haim et al. |
| 2007/0185540 A1 | 8/2007 | Ben-Haim et al. |
| 2007/0299320 A1 | 12/2007 | Policker et al. |
| 2008/0046062 A1 | 2/2008 | Camps et al. |
| 2008/0058889 A1 | 3/2008 | Ben-Haim et al. |
| 2008/0058891 A1 | 3/2008 | Ben-Haim et al. |
| 2008/0065168 A1 | 3/2008 | Bitton et al. |
| 2008/0077174 A1* | 3/2008 | Mische ........................ 606/198 |
| 2008/0178684 A1 | 7/2008 | Spehr |

| | | | |
|---|---|---|---|
| 2008/0188837 | A1* | 8/2008 | Belsky et al. ............. 604/890.1 |
| 2009/0062893 | A1 | 3/2009 | Spehr |
| 2009/0088816 | A1 | 4/2009 | Harel et al. |
| 2009/0118797 | A1 | 5/2009 | Kliger et al. |
| 2009/0131993 | A1 | 5/2009 | Rousso et al. |
| 2009/0204063 | A1 | 8/2009 | Policker et al. |
| 2009/0281449 | A1 | 11/2009 | Thrower et al. |
| 2010/0228105 | A1 | 9/2010 | Policker et al. |
| 2010/0305468 | A1 | 12/2010 | Policker et al. |
| 2010/0324644 | A1 | 12/2010 | Levi et al. |

FOREIGN PATENT DOCUMENTS

| | | |
|---|---|---|
| EP | 0129483 | 12/1984 |
| EP | 144705 | 6/1985 |
| EP | 1036545 | 9/2000 |
| EP | 1 447 052 | 8/2004 |
| JP | 2003/319945 | 11/2003 |
| JP | 2003319945 | 11/2003 |
| WO | WO 94/01172 | 1/1994 |
| WO | WO 97/25098 | 7/1997 |
| WO | WO 97/26042 | 7/1997 |
| WO | WO 97/31679 | 9/1997 |
| WO | WO 98/10830 | 3/1998 |
| WO | WO 99/03533 | 1/1999 |
| WO | WO 00/53257 | 9/2000 |
| WO | WO 01/10375 | 2/2001 |
| WO | WO 01/41671 | 6/2001 |
| WO | WO 01/66183 | 9/2001 |
| WO | WO 01/83019 | 11/2001 |
| WO | WO 01/91854 | 12/2001 |
| WO | WO 02/053093 | 7/2002 |
| WO | WO 02/082968 | 10/2002 |
| WO | WO 02/089655 | 11/2002 |
| WO | WO 03/020365 | 3/2003 |
| WO | WO 03/045493 | 6/2003 |
| WO | WO 2004/021858 | 3/2004 |
| WO | WO 2004/043280 | 5/2004 |
| WO | WO 2004/066903 | 8/2004 |
| WO | WO 2004/069330 | 8/2004 |
| WO | WO 2004/091361 | 10/2004 |
| WO | WO 2004/096337 | 11/2004 |
| WO | WO 2004/112563 | 12/2004 |
| WO | WO 2004/112883 | 12/2004 |
| WO | WO 2005/007232 | 1/2005 |
| WO | WO 2005/007237 | 1/2005 |
| WO | WO 2005/009288 | 2/2005 |
| WO | WO 2005/016181 | 2/2005 |
| WO | WO 2005/023081 | 3/2005 |
| WO | WO 2005/037152 | 4/2005 |
| WO | WO 2005/041749 | 5/2005 |
| WO | WO 2005/087310 | 9/2005 |
| WO | WO 2006/018851 | 2/2006 |
| WO | WO 2006/035446 | 4/2006 |
| WO | WO 2006/087712 | 8/2006 |
| WO | WO 2006/087717 | 8/2006 |
| WO | WO 2006/097934 | 9/2006 |
| WO | WO 2006/102626 | 9/2006 |
| WO | WO 2006/129321 | 9/2006 |
| WO | WO 2006/118790 | 11/2006 |
| WO | WO 2007/080595 | 7/2007 |
| WO | WO 2008/117296 | 10/2008 |
| WO | WO 2008/139463 | 11/2008 |
| WO | WO 2011/092710 | 8/2011 |

OTHER PUBLICATIONS

Lamb F.S. et al., "Cyclosporine augments reactivity of isolated blood vessels", Life Sciences, 40, pp. 2571-2578, 1987.

Johansson B. et al., "Static and dynamic components in the vascular myogenic response to passive changes in length as revealed by electrical and mechanical recordings from the rat portal vein", Circulation Research, 36, pp. 76-83, 1975.

Zelcer E. et al., "Spontaneous electrical activity in pressurized small mesenteric arteries", Blood Vessels, 19, pp. 301-310, 1982.

Schobel H.P. et al., "Preeclampsia—a state of sympathetic overactivity", New England Journal of Medicine, 335, pp. 148-1485, 1996.

Rosenpire A.J. et al., "Pulsed DC Electric Fields Couple to Natural NAD(P)H Oscillations in HT-1080 Fibrosarcoma Cells", Journal of Cell Science, 114(Pt. 8), pp. 1515-1520, Apr. 2001.

Gomis A. et al., "Oscillatory patterns of electrical activity in mouse pancreatic islets of Langerhans recorded in vivo", Pflugers Archiv European Journal of Physiology, Abstract vol. 432(3), pp. 510-515, 1996.

Soria B. et al., "Cytosolic calcium oscillations and insulin release in pancreatic islets of Langerhans", Diabetes Metab., 24(1), pp. 37-40, Feb. 1998.

Magnus G. et al., "Model of Beta-cell mitochondrial calcium handling and electrical activity. II. Mitochondrial variables", American Journal of Physiology, 274(4 Pt 1): C1174-1184, Apr. 1998.

Yamada, "Effects of drugs on electromechanical activities of the stomach and duodenum of conscious dogs", Nippon Heikatsukin Gakkai Zasshi. Feb. 1983;19(1):25-35. (abstract only).

Nadal A. et al., "Homologous and heterologous asynchronicity between identified alpha-, beta-, and delta-cells within intact islets of Langerhans in the mouse", Journal of Physiology, 517(Pt. 1), pp. 85-93, May 1999.

M D Robertson, et al, "The influence of the colon on postprandial glucagons-like peptide 1 (7-36) amide concentration in man", Journal of Endocrinology (1999) 161, 25-31.

J Schirra, et al, "Mechanisms of the antidiabetic action of subcutaneous glucagons-like peptide-1 (7-36) amide in non-insulin dependent diabetes mellitus", Journal of Endocrinology (1998) 156, 177-186.

T Vilsboll and Associates, Research design and methods, Diabetes, vol. 50, Mar. 2001, pp. 610-613.

Jeannie F. Todd, et al, "Subcutaneous glucagons-like peptide-1 improves postprandial glycaemic control over 3-week period in patients with early type 2 diabetes", Clinical Science (1998) 95, 325-329.

Daniel J. Drucker, "Development of glucagon-like peptide-1-based pharmaceuticals as therapeutic agents for the treatment of diabetes", Current Pharmaceutical Design, 2001, 7, 1399-1412.

Shemerovskii KA, "Effect of feeding on the activity of duodenal smooth muscle in dogs", Biull Eksp Biol Med. Oct. 1978;86(10):394-7. (Abstract only).

U.S. Appl. No. 60/742,365.

U.S. Appl. No. 10/237,263.

USPTO Office Action dated Jul. 28, 2008—U.S. Appl. No. 11/336,099.

USPTO Office Action dated Nov. 4, 2008—U.S. Appl. No. 11/336,099.

USPTO Office Action dated Aug. 6, 2009—U.S. Appl. No. 11/336,099.

USPTO Office Action dated Nov. 15, 2010—U.S. Appl. No. 11/336,099.

USPTO Office Action dated May 20, 2011—U.S. Appl. No. 11/336,099.

International Search Report and the Written Opinion Dated Sep. 2, 2011 From the International Searching Authority Re. Application No. PCT/IL 11/00116.

Article—Rey, et al—European Society of Gastrointestinal Endoscopy (ESGE), 2006, pp. 1047-1053.

U.S.P.T.O. Office Action dated Nov. 30, 2011, issued in U.S. Appl. No. 11/336,099.

Offica Action Dated May 10, 2012 in U.S. Appl. No. 10/599,015.

* cited by examiner

INGESTIBLE CAPSULE FOR APPETITE REGULATION

CROSS-REFERENCES TO RELATED APPLICATIONS

The present patent application claims the benefit of U.S. Provisional Patent Application 60/742,365 to Bitton, filed Dec. 5, 2005, entitled, "Ingestible capsule for appetite regulation," which is assigned to the assignee of the present patent application and is incorporated herein by reference.

FIELD OF THE INVENTION

The present invention relates generally to appetite regulation, and specifically to swallowable apparatus for appetite control and treating obesity.

BACKGROUND OF THE INVENTION

Obesity is a difficult to treat chronic condition defined by a body mass index (BMI=mass/height$^2$[kg/m$^2$]) greater than 30. For obese persons, excessive weight is commonly associated with increased risk of cardiovascular disease, diabetes, degenerative arthritis, endocrine and pulmonary abnormalities, gallbladder disease and hypertension. Additionally, such persons are highly likely to experience psychological difficulties because of lifestyle restrictions such as reduced mobility and physical capacity, due to back pain, joint problems, and shortness of breath. In severe cases, this can contribute to absenteeism and unemployment. Moreover, impairment of body image can lead to significant psychological disturbances. Repeated failures of dieting and exercise to resolve the problem of obesity can result in feelings of despair and the development of clinical depression.

Bariatric surgery is often recommended for persons suffering from morbid obesity. Preferably, the invasive treatment is accompanied by changes in lifestyle, such as improved regulation of eating habits and an appropriate exercise regimen. Such lifestyle changes are dependent upon the self-discipline and cooperation of the subject.

A book entitled, *Textbook of Gastroenterology,* 3rd edition, edited by Yamada (Lippincott, Williams & Wilkins), which is incorporated herein by reference, includes, in Chapter 10 thereof, a description of the physiology of gastric motility and gastric emptying.

An abstract entitled, "Gastric myoelectrical pacing as therapy for morbid obesity: Preliminary results," by Cigaina et al., retrieved on Dec. 24, 2000 from the Web-site http://www.med-online.com/transneuronix/Product/abstract.htm, which is incorporated herein by reference, describes a method for applying monopolar and bipolar gastric stimulation to achieve weight loss.

An abstract entitled, "Implantable gastric stimulator (IGS) as therapy for morbid obesity: Equipment, surgical technique and stimulation parameters," by Cigaina et al., retrieved on Dec. 24, 2000 from the Web-site http://www.med-online.com/transneuronix/Product/abstract.htm, which is incorporated herein by reference, describes techniques of electrical signal therapy designed to treat obesity.

PCT Publication WO 05/087310 to Harel et al., which is assigned to the assignee of the present application and is incorporated herein by reference, describes a method for glucose level control including providing at least one electrode adapted to apply an electric field to a pancreas, and applying an electric field to the pancreas using said at least one electrode such that blood glucose levels are significantly reduced and blood insulin levels are not significantly increased compared to a regular insulin response in a same person. In an embodiment, the electric field is applied using electrodes on opposite sides of the stomach, so that a main conductive pathway between the electrode, which cannot pass through the hollow of the stomach, circumvents the stomach and passes through a portion of the pancreas. Optionally, the electric field has little or no effect on other organs, such as the stomach.

PCT Publication WO 04/066903 to Gross et al., which is incorporated herein by reference, describes apparatus for drug administration, including an ingestible capsule holding the drug. An environmentally-sensitive mechanism is adapted to change a state thereof responsive to a disposition of the capsule within a gastrointestinal tract of a subject. A driving mechanism, in response to a change of state of the environmentally-sensitive mechanism, is adapted to drive the drug directly through an endothelial layer of the gastrointestinal tract. In an embodiment, the driving mechanism includes an electrode. In an embodiment, the capsule includes self-expansible portions, which, for some applications, are covered with electrodes for stimulating the walls of the gastrointestinal tract.

PCT Publication WO 05/009288 to Burnett et al., which is incorporated herein by reference, describes devices for intermittently and/or partially obstructing a pyloric valve. The devices generally include a support portion for preventing the device from passing through the pyloric valve and a tissue engagement portion for contacting tissue adjacent the pyloric valve to obstruct the valve. Some embodiments also include a positioning member extending from the issue engagement portion for helping position the device for obstructing the valve. Some embodiments are deliverable into the stomach through the esophagus, either by swallowing or through a delivery tube or catheter. Some embodiments self-expand within the stomach, while others are inflated or otherwise expanded. Some embodiments include one or more electrodes coupled with the device and removably attachable to stomach tissue, or electrodes formed over a surface of the device.

U.S. Patent Application Publication 2004/0162469 to Imran and PCT Publication WO 04/091361 to Imran et al., which are incorporated herein by reference, describe a device and method for mapping, diagnosing, and treating conditions of the intestinal tract, such as bleeding, ischemic or necrotic tissue, and presence of certain chemicals or substances. The device includes a capsule that passes through the intestinal tract and senses optical characteristics. A map of optical characteristics is derived to diagnose the condition. The capsule or subsequently-passed capsules may treat, further diagnose, or mark the intestinal tract at a determined location along its length.

U.S. Patent Application Publication 2004/008023 to Imran et al., which is incorporated herein by reference, describes a device for diagnosing and treating gastric disorders. A functional device resides within the subject's stomach and is secured to the stomach wall by an attachment device. The functional device may be a sensor for sensing various parameters of the stomach or stomach environment, or may be a therapeutic delivery device. The functional device in one embodiment provides a device for gastric electrical stimulation, wherein stimulating electrodes are secured to the wall of the stomach by the attachment device or otherwise. One device described includes at least one stimulating electrode in electrical contact with the stomach wall; an electronics unit containing the electronic circuitry of the device; and an attachment mechanism for attaching the device to the stomach wall. The functional devices may be programmed to respond to sensed information or signals. An endoscopic delivery system delivers the functional device through the esophagus and into the stomach where it is attached the stomach wall. The endoscopic instruments attach or remove the attachment devices and functional devices from the stomach and may be used to assist in determining the optimal attachment location.

U.S. Patent Application Publication 2005/0021101 to Chen et al., which is incorporated herein by reference, describes a method for regulating gastrointestinal action in a subject using a stimulatory electrode and a sensor to provide retrograde feedback control of electrical stimulation to the GI tract. Also described is a method for reducing weight in a subject, using a stimulatory electrode and a sensor to provide retrograde feedback control of electrical stimulation to the stomach. Further described is a method for providing electrical field stimulation to a gastrointestinal organ, as well as a method of providing an electrical potential gradient in a gastrointestinal organ. Still further described is a method for stimulating the vagus nerve of a subject. Additionally, described is a method of placing a device in the gastrointestinal tract or wall of a subject from the exterior of the subject, using a needle to insert the device.

U.S. Pat. No. 6,754,536 to Swoyer et al., which is incorporated herein by reference, describes a GI tract stimulator and/or monitor and/or implantable medical device comprising a housing enclosing electrical stimulation and/or monitoring circuitry and a power source, and an elongated flexible member extending from the housing to an active fixation mechanism, which is adapted to be fixed into the GI tract wall. After fixation, the elongated flexible member bends into a preformed shape that presses the housing against the mucosa so that forces that would tend to dislodge the fixation mechanism are minimized. The device is fitted into an esophageal catheter lumen with the fixation mechanism aimed toward the catheter distal end opening, whereby the bend in the flexible member is straightened. The catheter body is inserted through the esophagus into the GI tract cavity to direct the catheter distal end to the site of implantation and fix the fixation mechanism to the GI tract wall. The device is ejected from the lumen, and the flexible member assumes its bent configuration and lodges the hermetically sealed housing against the mucosa. For temporary use, the fixation mechanism can be made of a material that is degraded by stomach acid over time to release the GI tract stimulator or monitor device and allow it to pass through the GI tract.

U.S. Pat. No. 6,129,685 to Howard, which is incorporated herein by reference, describes apparatus and methods for regulating appetite by electrical stimulation of the hypothalamus and by microinfusion of an appropriate quantity of a suitable drug to a distinct site or region within the hypothalamus.

U.S. Pat. No. 4,823,808 to Clegg et al., which is incorporated herein by reference, describes a method for treating obesity, including receiving a physiological measurement and generating audio and/or visual feedback for the subject to hear and/or see. The feedback is used for purposes of teaching behavior modification.

U.S. Pat. No. 5,868,141 to Ellias, which is incorporated herein by reference, describes an endoscopic stomach insert for reducing a subject's desire to eat.

U.S. Pat. No. 6,067,991 to Forsell, U.S. Pat. No. 5,601,604 to Vincent, U.S. Pat. No. 5,234,454 to Bangs, U.S. Pat. No. 4,133,315 to Berman et al., U.S. Pat. No. 4,416,267 to Garren et al., and U.S. Pat. Nos. 4,592,339, 5,449,368, 5,226,429 and 5,074,868 to Kuzmak, which are incorporated herein by reference, describe mechanical instruments for implantation in or around the stomach of an obese subject.

U.S. Pat. No. 5,690,691 to Chen et al., which is incorporated herein by reference, describes a gastric pacemaker for treating obesity and other disorders. The pacemaker includes multiple electrodes which are placed at various positions on the gastrointestinal (GI) tract, and deliver phased electrical stimulation to pace peristaltic movement of material through the GI tract.

U.S. Pat. No. 5,423,872 to Cigaina, which is incorporated herein by reference, describes apparatus for applying electrical pulses to the distal gastric antrum of a subject, so as to reduce the motility of the stomach and to thereby treat obesity or another disorder.

U.S. Pat. Nos. 5,188,104 and 5,263,480 to Wernicke et al., which are incorporated herein by reference, describe a method for stimulating the vagus nerve of a subject so as to alleviate an eating disorder.

U.S. Pat. Nos. 6,104,955, 6,091,992, and 5,836,994 to Bourgeois, U.S. Pat. No. 6,026,326 to Bardy, and U.S. Pat. No. 3,411,507 to Wingrove, which are incorporated herein by reference, describe the application of electrical signals to the GI tract to treat various physiological disorders.

U.S. Pat. No. 5,979,449 to Steer, which is incorporated herein by reference, describes an oral appliance for appetite suppression.

U.S. Pat. No. 4,975,682 to Kerr et al., which is incorporated herein by reference, describes apparatus for food intake regulation which is external to the body and which is based upon the voluntary cooperation of the subject in order to be effective.

U.S. Pat. No. 5,861,014 to Familoni, U.S. Pat. No. 5,716,385 to Mittal et al., and U.S. Pat. No. 5,995,872 to Bourgeois, which are incorporated herein by reference, describe methods and apparatus for stimulation of tissue, particularly gastrointestinal tract tissue.

PCT Patent Publication WO 02/082968 to Policker et al., entitled, "Analysis of eating habits," which is incorporated herein by reference, describes apparatus and methods for detecting the occurrence of an eating event by a subject, and analyzing the quantity and characteristics of the food ingested.

U.S. Pat. No. 6,600,953 to Flesler et al., which is incorporated herein by reference, describes apparatus for treating a condition such as obesity. The apparatus includes a set of one or more electrodes, which are adapted to be applied to one or more respective sites in a vicinity of a body of a stomach of a subject. A control unit is adapted to drive the electrode set to apply to the body of the stomach a signal, configured such that application thereof increases a level of contraction of muscle tissue of the body of the stomach, and decreases a cross-sectional area of a portion of the body of the stomach for a substantially continuous period greater than about 3 seconds.

U.S. Patent Application Publication 2004/0059393 to Policker et al., which is incorporated herein by reference, describes a method for treating a subject, including receiving a sensor signal responsive to the subject eating, analyzing the sensor signal, and driving a current into tissue of the subject responsive to analyzing the signal. The current is typically driven into muscle tissue of the subject's stomach. Preferably, receiving the sensor signal includes sensing an electrical potential change generated responsive to contraction of a muscle such as a stomach muscle of the subject. In an embodiment, the sensor signal is analyzed with respect to the timing of ingestion, and a level of compliance of the subject with a desired ingestion schedule is determined. As appropriate, a parameter of the current driven into the tissue may be configured such that the application of the current to the tissue induces in the subject a sensation of satiety, discomfort, nausea, or vertigo.

U.S. Pat. No. 6,415,178 and PCT Patent Publication WO 98/10830 to Ben-Haim et al., which are incorporated herein by reference, describe various methods for controlling the behavior of muscle tissue, for example by blocking or altering the transmission of signals therethrough.

PCT Publication WO 05/007232 to Ben Haim et al., which is incorporated herein by reference, describes techniques for treating a subject, including applying an electrical signal to at least one stomach site of the subject. The electrical signal is configured to reduce a rise in a blood glucose level of the subject, in order to treat the subject.

U.S. Pat. No. 6,571,127 and PCT Publication WO 99/03533 to Ben-Haim et al., which are incorporated herein by reference, describe apparatus and methods for applying signals to smooth muscle so as to modify the behavior thereof. In particular, apparatus for controlling the stomach is described in which a controller applies an electrical field to electrodes on the stomach wall so as to modify the reaction of muscle tissue therein to an activation signal, while not generating a propagating action potential in the tissue. In the context of the present patent application and in the claims, the use of such a non-excitatory signal to modify the response of one or more cells to electrical activation thereof, without inducing action potentials in the cells, is referred to as Excitable-Tissue Control (ETC). Use of an ETC signal is described with respect to treating obesity, by applying the ETC signal to the stomach so as to delay or prevent emptying of the stomach. In addition, a method is described for increasing the motility of the gastrointestinal tract, by applying an ETC signal to a portion of the tract in order to increase the contraction force generated in the portion and the stretching of nearby tissue.

U.S. Pat. No. 6,709,388 to Mosse et al., which is incorporated herein by reference, describes a self-propelling device adapted to travel through a passage having walls containing contractile tissue, the device comprising a body and at least one contractile tissue-stimulating means for stimulating the walls to urge the device selectively. The stimulating means may be electrodes, and the passage can be the gut of an animal or human. The device is described as being particularly useful as an enteroscope.

PCT Publication WO 97/31679 to Dirin et al., which is incorporated herein by reference, discloses that USSR Inventor's Certificate No. 1223922, Int. C1, A 61 N 1/36, Bulletin No. 14, by Pekarasky et al., entitled "Gastrointestinal tract electrostimulator," which is incorporated herein by reference, describes a swallowable capsule adapted for electrostimulation of the alimentary tract, as post-surgical therapy, as a prophylactic measure of treating alimentary tract diseases, or for the promotion of peristalsis, which is further adapted for the dispensing of medication.

PCT Publication WO 97/26042 to Terekhin et al., which is incorporated herein by reference, describes medical equipment that can be used, for example, in post-surgical therapy in outpatient clinics and in hospitals, as well as a prophylactic measure for treating alimentary tract diseases. The equipment is described as an electrical stimulant containing a capsule, in which are located consecutively-connected units for testing parameters of an external medium and a pulse driver, connected to a power supply. Electrodes are provided on the external surface of the capsule, and total in number (2+n), wherein n=0, 1, 2, . . . .

PCT Publication WO 97/31679 to Dirin et al., which is incorporated herein by reference, describes electrostimulation of the gastrointestinal tract. Apparatus is described comprising an olive-like or ovate-cylindrical body member in which at least a part of opposed hemispheres is made conducting and forms a pair of electrodes, as well as a pulse generator and an electric power supply source disposed inside said body member. The apparatus is described as comprising an electrode and means for cyclically reversing the polarity of pulses on the electrodes. Electrostimulation efficiency of the device is described as being independent of opposite preferential orientations of its body member within a given visceral organ of a human being or animal.

PCT Publication WO 04/066903 to Gross et al., which is incorporated herein by reference, describes apparatus for drug administration, including an ingestible capsule. The capsule includes a drug stored by the capsule. An environmentally-sensitive mechanism is adapted to change a state thereof responsive to a disposition of the capsule within a gastrointestinal tract of a subject. A driving mechanism, in response to a change of state of the environmentally-sensitive mechanism, is adapted to drive the drug directly through the endothelial layer of the gastrointestinal tract.

PCT Publication WO 06/018851 to Kliger et al., which is incorporated herein by reference, describes gastric apparatus including one or more sensors, adapted to generate respective sensor signals responsive to activity of a gastrointestinal tract of a subject. A control unit is described as being adapted to receive and analyze the sensor signals and to determine that an eating event has occurred, responsive to at least one of the sensor signals and a threshold. The control unit identifies an aspect of at least one of the sensor signals deriving from rhythmic activity of the gastrointestinal tract that is not indicative or current eating by the subject, and modifies the threshold responsive to the aspect of the signals that derives from activity that is not indicative of current eating. For some applications, the control unit is described as being adapted to modify the threshold if the aspect is indicative of a migrating motor complex (MMC). Other embodiments are also described.

SUMMARY OF THE INVENTION

In some embodiments of the present invention, an ingestible food intake regulation system comprises an electrode device and an ingestible capsule. The capsule is adapted to hold the electrode device during ingestion of the system by a subject, and to release the electrode device in a stomach of the subject. The electrode device comprises one or more support elements, which comprise a plurality of electrodes distributed along the support elements. The support elements are adapted to expand upon release in the stomach, such that at least a portion of the electrodes comes in contact with a wall of the stomach at least a portion of the time that the electrodes are in the stomach. Typically, at least a portion of the electrodes comes in contact with the stomach wall most of the time, e.g., substantially all of the time, that the electrodes are in the stomach. (The electrode device may move over time while it is in the stomach, in which case different electrodes will be in contact with the wall at different times.) The electrode device further comprises a control unit that is adapted to increase satiety of the subject by driving the electrodes to apply an electrical signal to the stomach wall. The electrodes and control unit are typically adapted to remain in the stomach for at least 24 hours, such as for at least one week, one month, or three months.

The system is typically useful for treating eating disorders, such as obesity and anorexia. For some applications, the control unit is adapted to configure the applied electrical signal to treat diabetes of the subject, typically by reducing glucose levels, in addition to or instead of configuring the electrical signal to increase satiety of the subject. As appropriate, signal protocols and/or other techniques described in the patents, patent applications, and articles incorporated herein by reference are adapted for use to facilitate use of the electrode device for these treatments. For example, techniques described herein may be used in combination with techniques for reducing glucose levels described in the above-mentioned PCT Publication WO 05/087310.

In some embodiments of the present invention, the control unit is adapted to detect eating by the subject, and to apply the electrical signal responsively to such detection. The control unit typically detects eating by detecting: (a) changes in the rate of slow waves in an antrum of the stomach indicative of eating, (b) a change in the pH of the stomach indicative of eating, (c) the onset of contractions of the stomach indicative of eating, and/or (d) the filling of the stomach.

In some embodiments of the present invention, an external communication device is configured to wirelessly communicate with the control unit, typically using radio frequency transmission.

For some applications, the communication is bidirectional. For example, the control unit may transmit data indicative of a state of the stomach to the external communication device, and the external communication device, in turn, transmits data to the control unit. Typically, the external communication device comprises an input device, e.g., a button or a switch, configured to receive input from the subject, e.g., a start time of eating. The input is then transmitted to the control unit. In response to the transmitted input, the control unit drives the electrodes to apply the electrical signal to the stomach wall.

For some applications, the control unit transmits to the external communication device a sensed indication regarding a diet of the subject, such as a start time of eating, an end time of eating, a duration of gastric activity, or an indication of a quality of ingested food (e.g., solid or liquid, or caloric content). This transmitted indication in turn facilitates physician- or subject-monitoring of the subject's diet to support weight loss in a manner suitable for each individual subject. Alternatively or additionally, one or more transmitted indications are used to generate a new stimulation protocol for transmission from the external communication device to the control unit. Typically, the external communication device transmits data, e.g., the stimulation protocol itself or an indication of a desired protocol (e.g., "Protocol #7"), to the control unit, in response to the transmission of the sensed indication from the control unit. Protocols may include, for example, particular signal application schedules, or a variety of thresholds of responsiveness to eating detection.

In some embodiments of the present invention, the communication between the control unit and the external communication device is unidirectional. The external communication device is configured to generate a stimulation protocol for the plurality of electrodes, and transmit data representing the protocol, from outside a body of the subject to the control unit.

For some applications in which the communication is unidirectional, the control unit transmits an indication of a state of the stomach to the external communication device, to be conveyed to the subject or a physician. The indication of the state of the stomach provides the subject or the physician with an assessment of the response of the subject, e.g., number of meals per day, to the applied electrical signal. Additionally, the indication allows for proper monitoring of the diet of the subject, to engender weight loss.

In some embodiments of the present invention, the control unit communicates with other external programming devices which enable programming, interrogation and telemetry, from outside the body of the subject.

In some embodiments of the present invention, the capsule is not ingestible, but is instead configured to be chronically implanted in the stomach of the subject. Typically, the capsule comprising a securing mechanism is endoscopically guided into the stomach of the subject. The securing mechanism is then endoscopically mounted onto the stomach wall, and the support elements place the electrodes in contact with the stomach wall.

For some applications, the capsule designated for chronic implantation, or a gastric stimulator known in the art, is designated for implantation following an initial trial using an ingestible capsule as described herein. Successful results from the ingestible capsule (e.g., weight loss or blood sugar control) are used as an indication that electrical signal application to the subject's stomach justify chronic implantation. Similarly, subjects who do not respond positively to the ingestible capsule are typically referred for other (e.g., non-electrical) forms of weight control.

In some embodiments of the present invention, the control unit is adapted to drive the electrodes to apply an enhancement signal, such as an Excitable-Tissue Control (ETC) signal and/or an excitatory signal, to the stomach wall. Typically, but not necessarily, the control unit configures the signal to modulate (e.g., decrease or increase) a rate of slow wave propagation in the stomach. For some applications, the control unit configures the signal to modulate contraction of muscles of the stomach so as to increase the satiety of the subject. For example, the enhancement signal may induce contractions and/or increase or otherwise modify the contraction forces generated by muscles of the stomach. Alternatively or additionally, the enhancement signal may be configured to include a component that modulates nervous activity (e.g., using techniques described in one or more of the patents, patent applications, or articles incorporated herein by reference).

In some embodiments of the present invention, the enhancement signal is applied to muscle in one portion of the stomach, so as to induce and/or modify a contraction of the stimulated muscle which, in turn, causes stretching of stretch-receptors in an adjacent portion of the stomach. This form of contraction-medicated stretching simulates the normal satiety signaling of the stomach's stretch-receptors, without the subject having eaten the quantities of food which would normally be required to trigger this satiety response.

For some applications, the enhancement signal is applied so as to modify a contraction pattern of some of the stomach's muscles, in order to reduce the cross-sectional area of a portion of the stomach. The narrow ring thereby generated reduces the volume of a region of the stomach, and increases the sensation of satiety felt by the subject compared to that which would be felt without the application of this embodiment of the invention. For example, the enhancement signal may cause an "indenting" of the stomach wall, whereby food is limited in its ability to vacate the esophageal region of the stomach. Consequently, this portion of the stomach is stretched more than usual for the volume of food ingested, and an earlier sensation of satiety is induced. This embodiment thus employs electrical signals to cause a narrowing of the stomach analogous to that produced mechanically by gastric bands known in the art.

Alternatively or additionally, the enhancement signal is applied, prior to and/or during a meal, so as to reduce the overall size of the stomach, thereby increasing the tension in the wall of the stomach when food is in the stomach. This increased tension typically yields a corresponding increase in the subject's sensation of satiety, and thus sub substantially reduces the likelihood of the subject overeating.

In some embodiments of the present invention, the ingestible capsule is configured to be administered prior to eating a meal. A plurality of external electrodes are coupled to an exterior surface of the capsule. The capsule is configured to move about within the stomach for the duration of the meal including the time interval of digestion of the meal within the stomach, such that at least a portion of the plurality of electrodes comes in contact with a wall of the stomach at least a portion of the time that the capsule is in the stomach. The capsule is configured to remain in the stomach for the duration of the meal and pass naturally therefrom following the meal. In these embodiments, the capsule is typically, but not necessarily, not expandable (e.g., support elements do not expand to bring electrodes into contact with the stomach wall).

Further alternatively or additionally, repeated application of the enhancement signal engenders a long-term shortening of muscle fibers of the stomach, and, consequently, a reduction of the size of the stomach, even at times when the signal is not being applied. Thus, for example, the enhancement signal may be applied, intermittently throughout the day, over a period of days, weeks, or months, so as to induce desired structural changes in the stomach which last, preferably, for at least several days or weeks after removal of the signal. Advantageously, due to the stomach's reduced size, it is typically stretched during and after a meal to a greater extent than would occur without application of the enhancement signal, and thus greater sensations of satiety are felt by the subject. Optionally, the signal may be applied when the subject's stomach is expected to be relatively empty (e.g., each morning for one hour prior to the subject waking up), so as to maximize the extent to which the muscle fibers are able to shorten in response to the signal.

For some subjects, it is desirable to apply the enhancement signal according to a schedule, whereby constriction of the stomach induces a feeling of satiety at times when the subject might choose to eat but should not be eating. At other times, e.g., when the subject is sleeping, the signal it typically not applied. Alternatively or additionally, the enhancement signal is (a) applied during one or more meals during the day, so as to reduce the subject's appetite during those meals, and (b) removed during meals eaten during the remainder of the day, so as to prevent nutritional deficiencies which might occur in some subjects from any inappropriate, excessive use of the signals described herein.

For some applications, the feeling of satiety is induced by applying electrical signals which enhance the mobility of chyme from the fundus to the antrum of the stomach, where stretch-receptor signals are generally generated to a greater extent for a given quantity of food than in the fundus.

There is therefore provided, in accordance with an embodiment of the present invention, a method for treating a subject, including:

administering to the subject an ingestible capsule containing one or more flexible support elements adapted to expand while in a stomach of the subject, thereby bringing a plurality of electrodes into contact with a wall of the stomach; and driving the electrodes to apply an electrical signal to the stomach wall at first and second times, the second time at least 24 hours after the first time.

In an embodiment, driving the electrodes includes modulating nervous activity of the subject.

In an embodiment, the method includes sensing a parameter in a vicinity of the capsule, and transmitting an indication of the parameter from the capsule to a site outside of the subject.

In an embodiment, administering the ingestible capsule includes administering the capsule prior to eating by the subject.

In an embodiment, the method includes receiving an input from the subject indicative of the subject eating, and applying the signal includes applying the signal in response to receiving the input.

In an embodiment, driving the electrodes includes enhancing mobility of chyme within the stomach.

In an embodiment, driving the electrodes includes modulating a blood glucose level of the subject by stimulating a non-gastric organ.

In an embodiment, driving the electrodes includes modulating a blood glucose level of the subject by generating an electrical field within the stomach that directly stimulates a pancreas of the subject.

In an embodiment, driving the electrodes includes modulating a blood-hormone level associated with pancreatic activity.

In an embodiment, driving the electrodes includes indirectly modulating pancreatic activity by modulating efferent signaling to a pancreas of the subject.

In an embodiment, driving the electrodes includes driving the electrodes to apply an Excitable-Tissue Control (ETC) signal to the stomach wall.

In an embodiment, the method includes applying the electrical signal to the wall of the stomach at at least one time between the first and second times.

In an embodiment, applying the electrical signal includes applying the signal in response to a detection of the stomach being substantially empty.

In an embodiment, driving the electrical signal includes:
measuring a parameter of a vicinity of the electrodes; and
in response to the measuring, driving the electrodes to apply the electrical signal to the stomach wall.

In an embodiment, driving the electrodes includes modulating a rate of slow wave propagation in the stomach.

In an embodiment, driving the electrodes includes reducing a likelihood of the subject overeating.

In an embodiment, reducing the likelihood of the subject overeating includes increasing tension in a wall of the stomach by reducing an overall size of the stomach.

In an embodiment, driving the electrodes includes shortening muscle fibers of the stomach in response to the driving.

In an embodiment, shortening the muscle fibers includes maximizing the shortening by driving the electrodes to apply the electrical signal when the stomach is substantially empty.

In an embodiment, driving the electrodes includes configuring the signal to modulate a parameter of a contraction generated by stomach muscle of the subject.

In an embodiment, driving the electrodes includes configuring the signal to modulate a contraction force generated by stomach muscle.

In an embodiment, modulating the parameter includes increasing satiety of the subject.

In an embodiment, the method includes transmitting data to the ingestible capsule, from outside a body of the subject, subsequent to administering the capsule.

In an embodiment, transmitting the data includes transmitting using radio frequency transmission.

In an embodiment, transmitting the data includes transmitting a start time of eating.

In an embodiment, transmitting the data includes transmitting a termination time of eating.

In an embodiment, transmitting the data includes transmitting an indication of a strength of the electrical signal selected from a group consisting of: signal amplitude, frequency, and duty cycle.

In an embodiment, the method includes receiving an indication of a state of the subject from the ingestible capsule, and transmitting includes transmitting the data to the ingestible capsule in response to the received indication.

In an embodiment, driving the electrodes includes inducing a structural change in the stomach by repeated application of the electrical signal.

In an embodiment, repeated application of the electrical signal includes conditioning muscle fibers of the stomach.

In an embodiment, conditioning the muscle fibers includes engendering a long-term shortening thereof.

In an embodiment, repeated application of the electrical signal includes reducing an overall size of the stomach.

In an embodiment, repeated application of the signal includes applying an enhancement signal a plurality of times during a day.

In an embodiment, repeated application of the signal includes applying the signal during each of at least three successive days.

In an embodiment, repeated application of the signal includes applying the signal during each of at least two successive weeks.

In an embodiment, applying the electrical signal includes applying the signal according to a schedule while the subject is awake.

In an embodiment, applying the signal according to a schedule includes inducing a feeling of satiety.

In an embodiment, driving the electrodes to apply the electrical signal includes configuring the electrical signal to increase satiety of the subject.

In an embodiment, driving the electrodes to apply the electrical signal includes:
detecting eating by the subject; and
driving the electrodes responsively to the detection of the eating.

In an embodiment, detecting eating by the subject includes a method selected from the group consisting of:
detecting a change in a rate of slow waves in an antrum of the stomach indicative of eating;
detecting a change in a pH of the stomach indicative of eating;
detecting an onset of contractions of the stomach indicative of eating; and
detecting a filling of the stomach.

In an embodiment, detecting eating by the subject includes detecting an increase beyond a threshold level.

In an embodiment, detecting eating by the subject includes:
identifying a migrating motor complex (MMC) characterized by a change in an electrical activity of an antrum of the subject; and
modulating a threshold level of the eating detection in response thereto.

There is also provided, in accordance with an embodiment of the present invention, a method for treating a subject, including:
administering to the subject an ingestible capsule containing one ore more flexible support elements adapted to expand while in a stomach of the subject, thereby bringing a plurality of electrodes into contact with a wall of the stomach;
driving the electrodes to apply an electrical signal to the stomach wall;
assessing a response of the subject to the applied electrical signal; and
setting a protocol in response to the assessing.

In an embodiment, setting the signal protocol includes setting a protocol for signal application by the ingestible capsule.

In an embodiment, setting the signal protocol includes setting a protocol for signal application by another ingestible capsule.

In an embodiment, setting the signal protocol includes setting a protocol for signal application by chronically-implanted electrodes.

In an embodiment, assessing the response includes determining an indication that electrical signal application to the subject's stomach produces weight loss.

In an embodiment, the method includes chronically implanting electrodes within the subject in response to the indication.

There is further provided, in accordance with an embodiment of the present invention, apparatus for treating a subject including:
a plurality of electrodes;
one or more flexible support elements, which are coupled to the electrodes, and are adapted to expand in a stomach of a subject, such that at least a portion of the electrodes comes in contact with a wall of the stomach at least a portion of the time that the electrodes are in the stomach, the support elements adapted to remain in the stomach for at least 24 hours;
a control unit, adapted to drive the electrodes to apply an electrical signal to the stomach wall; and
an ingestible capsule, adapted to hold the support elements, electrodes, and control unit during ingestion of the capsule by the subject, and to release the support elements, electrodes, and control unit in the stomach.

In an embodiment, the control unit and the electrodes are configured to remain in the stomach for at least one week.

In an embodiment, the control unit and the electrodes are configured to remain in the stomach for at least one month.

In an embodiment, the control unit is adapted to configure the electrical signal to reduce a blood glucose level of the subject.

In an embodiment, the control unit is configured to configure the electrical signal to modulate activity of a pancreas of the subject.

In an embodiment, the control unit is adapted to drive the electrodes to apply an Excitable-Tissue Control (ETC) signal to the stomach wall.

In an embodiment, the ingestible capsule includes a material configured to dissolve in the stomach.

In an embodiment, the support elements include electrically conductive sections which are configured to function as electrodes.

In an embodiment, the plurality of electrodes include one or more local sense electrodes.

In an embodiment, the apparatus includes at least one physiological sensor, and the control unit is configured to drive the electrodes in response to a signal from the physiological sensor.

In an embodiment, the apparatus includes at least one mechanical sensor, and the control unit is configured to drive the electrodes in response to a signal from the mechanical sensor.

In an embodiment, the support elements are configured to remain expanded for a time period, and to collapse at the end of the time period, facilitating passage of the apparatus from the stomach.

In an embodiment, the support elements are configured to expand in a manner as to define a sphere if allowed to fully expand.

In an embodiment, the one or more support elements include a helically-shaped support element when expanded.

In an embodiment, the support elements include a dissolvable material configured to dissolve and allow passage of the apparatus from the stomach.

In an embodiment, the control unit is adapted to configure the electrical signal to increase satiety of the subject.

In an embodiment, the control unit is adapted to detect eating by the subject, and to drive the electrodes to increase the satiety of the subject responsively to the detection of the eating.

In an embodiment, the apparatus includes an eating sensor coupled to the control unit and configured to detect eating by detecting a change in a rate of slow waves in an antrum of the stomach, indicative of eating.

In an embodiment, the apparatus includes a physiological sensor coupled to the control unit and configured to detect eating by detecting a change in a pH of the stomach, indicative of eating.

In an embodiment, the apparatus includes a mechanical sensor coupled to the control unit and configured to detect eating by detecting an onset of a contraction of the stomach, indicative of eating.

In an embodiment, the apparatus includes a local sense electrode coupled to the control unit and configured to detect eating by detecting a filling of the stomach.

In an embodiment, the control unit is adapted to receive a signal indicative of possible eating by the subject, determine whether the signal exceeds a threshold level, and drive the electrodes to apply the signal responsively to the signal indicative of possible eating being beyond the threshold.

In an embodiment, the control unit is configured to recognize migrating motor complex (MMC) activity and to modulate the threshold level in response thereto.

In an embodiment, the apparatus includes an external communication device configured to wirelessly communicate with the control unit.

In an embodiment, the external communication device is configured to transmit data representing a stimulation protocol for the plurality of electrodes, from outside a body of the subject to the control unit.

In an embodiment, the external communication device includes an input device configured to receive input from the subject, and the communication device is configured to transmit the input to the control unit.

In an embodiment, the external communication device is configured to receive from the control unit a transmission indicative of a state of the stomach.

In an embodiment, the external communication device is configured to transmit data to the control unit, in response to the transmission from the internal control unit.

In an embodiment, the external communication device is configured to convey a state of the stomach to the subject in response to the transmission from the control unit.

There is yet further provided, in accordance with an embodiment of the present invention, apparatus for treating a subject, including:

an ingestible capsule configured to be ingested prior to eating a meal and coupled to a plurality of electrodes at an exterior surface of the capsule, the capsule is configured to move about within a stomach of the subject, such that at least a portion of the electrodes comes in contact with a wall of the stomach at least a portion of the time that the capsule is in the stomach; and a control unit, adapted to drive the electrodes to reduce an appetite of the subject by applying an electrical signal to the stomach wall.

In an embodiment, the capsule is configured to remain in the stomach for the duration of the meal, and pass naturally therefrom following the meal.

There is still further provided, in accordance with an embodiment of the present invention, apparatus for treating a subject, including:

a plurality of electrodes;

one or more flexible support elements, which are coupled to the electrodes, and are adapted to expand in a stomach of a subject, such that at least a portion of the electrodes comes in contact with a wall of the stomach;

a control unit, adapted to drive the electrodes to apply an electrical signal to the stomach wall; and a securing mechanism, configured to be endoscopically mounted to the stomach wall, and to maintain the support elements, electrodes, and control unit in the stomach.

There is additionally provided, in accordance with an embodiment of the present invention, a method for treating a subject, including:

administering to the subject an ingestible capsule containing one or more flexible support elements adapted to expand while in a stomach of the subject, thereby bringing a plurality of electrodes into contact with a wall of the stomach; and driving the electrodes to apply an electrical signal to the stomach wall at first and second times, the second time at least 24 hours after the first time.

In an embodiment, driving the electrodes to apply the electrical signal includes configuring the electrical signal to increase satiety of the subject. For some applications, driving the electrodes to apply the electrical signal includes detecting eating by the subject, and driving the electrodes responsively to the detection of the eating.

In an embodiment, driving the electrodes includes driving the electrodes to apply an Excitable-Tissue Control (ETC) signal to the stomach wall.

For some applications, the method including applying the electrical signal to the wall of the stomach at at least one time between the first and second times.

There is further provided, in accordance with an embodiment of the present invention, apparatus for treating a subject, including:

a plurality of electrodes;

one or more flexible support elements, which are coupled to the electrodes, and are adapted to expand in a stomach of a subject, such that at least a portion of the electrodes comes in contact with a wall of the stomach at least a portion of the time that the electrodes are in the stomach, the support elements adapted to remain in the stomach for at least 24 hours;

a control unit, adapted to drive the electrodes to apply an electrical signal to the stomach wall; and an ingestible capsule, adapted to hold the support elements, electrodes, and control unit during ingestion of the capsule by the subject, and to release the support elements, electrodes, and control unit in the stomach.

The present invention will be more fully understood from the following detailed description of the embodiments thereof, taken together with the drawings, in which:

DETAILED DESCRIPTION OF EMBODIMENTS

Figures 1A, 1B:
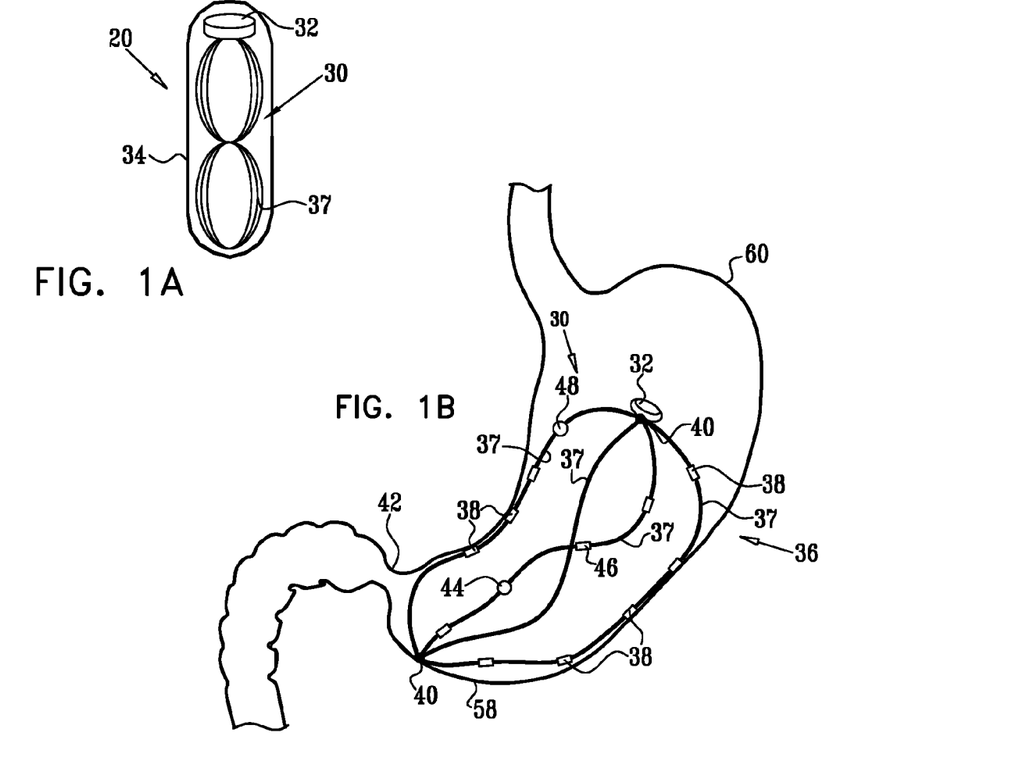
FIGS. 1A-C are schematic illustrations of an ingestible food intake regulation system, in accordance with respective embodiments of the present invention.
Figure 1C:
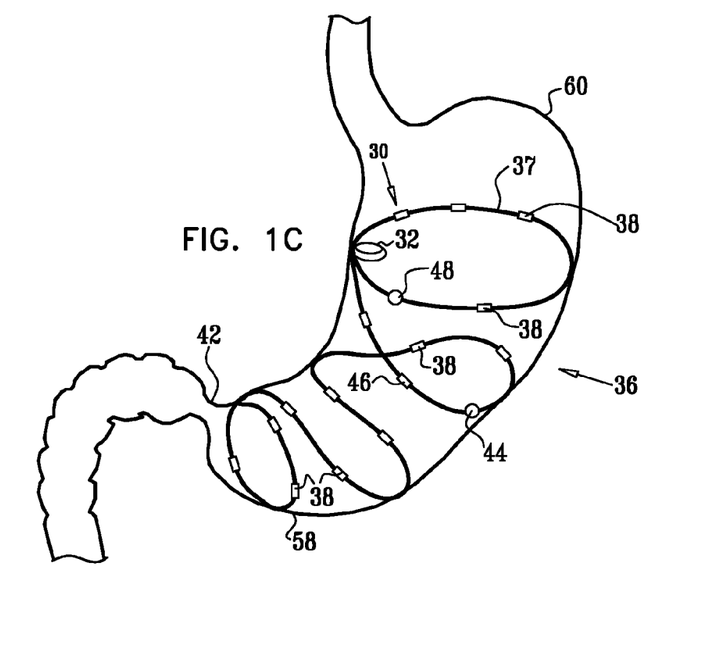

FIGS. 1A-C are schematic illustrations of an ingestible food intake regulation system 20, in accordance with respective embodiments of the present invention. System 20 comprises an electrode device 30 and an ingestible capsule 34. As shown in FIG. 1A, capsule 34 is adapted to hold electrode device 30 prior to ingestion of system 20 by a subject, and to release the electrode device in a stomach 36 of the subject, as shown in FIGS. 1B and 1C. Capsule 34 typically comprises a material (e.g., a pH-sensitive material) that dissolves in the stomach, thereby releasing electrode device 30. Suitable materials are well known in the art of oral drug delivery.

Electrode device 30 comprises a control unit 32 and one or more elongated flexible support elements 37. Support elements 37 are externally electrically insulated. For example, they may comprise a non-conductive coating, such as Teflon. Each of support elements 37 typically comprises a wire, which provides structure and electrically couples a plurality of electrodes 38, which are distributed along the support element, to control unit 32. Support elements 37 are adapted to expand upon release in stomach 36, such that at least a portion of the electrodes comes in contact with a wall of stomach 36 at least a portion of the time that electrode device 30 is in stomach 36. Typically, at least a portion of the electrodes comes in contact with the stomach wall most of the time, e.g., at least 50%, 75%, 95%, or 99% of the time, or substantially all of the time, that the electrodes are in stomach 36.

For some applications, electrodes 38 comprise ring electrodes, surrounding support elements 37, as shown in FIGS. 1B and 1C. Alternatively, the electrodes comprise exposed electrically-conductive sections of support elements 37 (not shown), or other electrodes known in the art. Electrode device 30 typically comprises a large number of electrodes 38, e.g., at least 30, 40, or 50 electrodes 38, so that a plurality of electrodes 38 remain in contact with the wall of the stomach at substantially all times. System 20 in configured so that a first subset of electrodes 38 and/or the case of control unit 32 serve as anodes, and a second subset of electrodes 38 and/or the case of control unit 32 serve as cathodes. For some applications, control unit 32 selects which electrodes serve as cathodes and anodes responsively to measurements made by all or a portion of the electrodes when they are configured to function as local sense electrodes 46, as described hereinbelow.

For some applications, electrode device 30 comprises a plurality of support elements 37 that are coupled to one another by one or more coupling elements 40, as shown in FIG. 1B. For example, support elements 37 may be configured to generally define a sphere if allowed to fully expand. However, the wall of the stomach prevents full expansion, causing a large portion of support elements 37, and thus electrodes 38, to come in contact with the stomach wall. Alternatively, electrode device 30 comprises one or more generally helically-shaped support elements 37, as shown in FIG. 1C. Other configurations of electrode device 30 will be evident to those skilled in the art who have read the present application, and are within the scope of the present invention.

Electrode device 30 is typically adapted to remain in stomach 36 for a predetermined estimated time period of at least 24 hours, such as for at least one week, one month, or three months. Typically, electrode device 30 remains in stomach 36 because electrode device 30, while expanded, is too large to pass through a pylorus 42. Typically, after passage of the predetermined estimated time period, at least a portion of electrode device 30 dissolves or comes apart, such that the components of electrode device 30 are able to pass through pylorus 42 and the intestine. For some applications, coupling elements 40 are adapted to dissolve after passage of the predetermined estimated time period. For example, coupling elements 40 may comprises chitin, and/or another non-toxic slowly-dissolvable material with a high strength. Alternatively or additionally, support elements 37 comprise a material adapted to dissolve after passage of the predetermined estimated time period.

In an embodiment of the present invention, electrode device 30 comprises at least one physiological sensor 44, one or more local sense electrodes 46, and/or at least one mechanical sensor 48. Sensor 44 is adapted to sense a physiological parameter of stomach 36, such as pH. Typically, some or all of electrodes 38 are adapted to serve as local sense electrodes 46, in order to sense electrical parameters of stomach 36, at least a portion of the time. Alternatively or additionally, dedicated electrodes serve as local sense electrode 46. Mechanical sensor 48 is adapted to sense mechanical properties of stomach 36. For example, mechanical sensor 48 may comprise an accelerometer, force transducer, strain gauge, or pressure gauge.

Reference is again made to FIG. 1A. For some applications, support element 37, while in an uncompressed position prior to placement in capsule 34, is shaped so as do define a generally circular loop. For placement in capsule 34, element 37 is folded by twisting opposite sides of the loop 180 degrees, so as to form a figure-8. The opposite loops of the figure-8 are brought together by folding the figure-8 over its central "X", so as to form a double-looped circle. This folding procedure is repeated several times. Element 37 is then placed in capsule 34, either in a figure-8 configuration, as shown in FIG. 1A, or in a circular configuration (not shown).

For some applications, an ingestible capsule is administered prior to eating a meal. Unlike the configuration shown in FIGS. 1A-C, a plurality of electrodes are coupled to an exterior surface of the capsule, and are typically not coupled to support elements 37. A time period of electrostimulation of stomach 36 by the plurality of external electrodes coupled to the capsule is limited to the duration of the meal and/or digestion of the meal. Increased satiety, leading to a decrease in food intake is, therefore, typically achieved while the subject is eating.

The capsule typically moves about within stomach 36 of the subject, such that at least a portion of the electrodes comes in contact with a wall of stomach 36 at least a portion of the time that the capsule is in stomach 36. Typically, at least a portion of the electrodes comes in contact with the stomach wall most of the time, e.g., at least 50%, 75%, 95%, or 99% of the time, or substantially all of the time, that the capsule is in stomach 36. The capsule is configured to remain in stomach 36 for the duration of the meal and pass naturally from stomach 36 following the meal.

Figure 2:
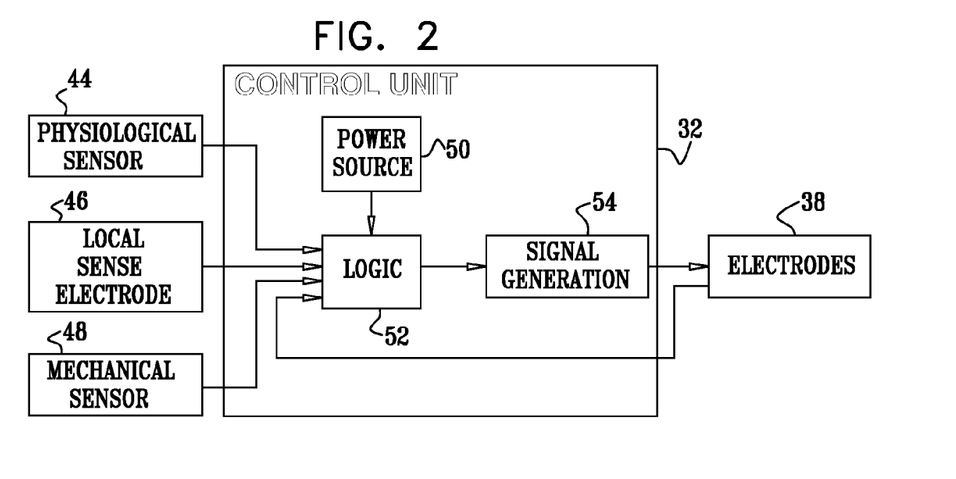
FIG. 2 is a schematic block diagram illustrating details of a control unit of the system of FIGS. 1A-C, in accordance with an embodiment of the present invention.

Reference is made to FIG. 2, which is a schematic block diagram illustrating details of control unit 32, in accordance with an embodiment of the present invention. Control unit 32 is powered by a power source 50, which may comprise, for example, a battery and/or a coil inductively coupled to an external power supply. Typically, control unit 32 receives signals from one or more of physiological sensor 44, local sense electrode 46, mechanical sensor 48, and electrodes 38. These sensors and electrodes are typically adapted to provide a logic unit 52 of the control unit with information about food ingestion and/or the present state of stomach 36.

For some applications, logic unit 52 determines each time that the subject swallows food, or each time that stomach 36 begins to contract in response to a threshold level of ingested food. For example, logic unit 52 may filter and process the output of mechanical sensor 48, so as to identify mechanical activity of the gastrointestinal tract indicative of eating. (It is to be understood in the context of the present patent application and in the claims that the terms "food" and "eating" apply equally to "liquids" and "drinking.")

Control unit 32 is adapted to increase satiety of the subject by driving electrodes 38 to apply an electrical signal to a wall of stomach 36. Logic unit 52 actuates a signal generation unit 54 to generate the electrical signal that is applied by electrodes 38. Signal generation unit 54 comprises amplifiers, isolation units, and/or other standard circuitry known in the art of electrical signal generation.

In an embodiment of the present invention, control unit 32 is adapted to detect eating by the subject, and to apply the electrical signal responsively to such detection. The control unit typically detects eating by detecting: (a) changes in the rate of slow waves in an antrum 58 of stomach 36 indicative of eating, (b) a change in the pH of stomach 36 indicative of eating, (c) the onset of contractions of stomach 36 indicative of eating, and/or (d) the filling of stomach 36. For some applications, the onset of eating or drinking is detected only by monitoring electrical changes in stomach 36. For some applications, electrode device 30 comprises a plurality of physiological sensors 44 and/or mechanical sensors 48, which generally reduces the likelihood of false indications of eating activity.

For some applications, control unit 32 is adapted to change one or more of the threshold values in response to a physiological event that has a tendency to cause false indications of eating activity. For example, a phenomenon known as the migrating motor complex (MMC) is characterized by a change in rhythm of antral electrical activity. This change in antral electrical activity is largely unrelated to eating, but can lead to false indications of eating activity. Since MMC activity lasts about 10 minutes and appears in a cyclical manner with a period of about 40 minutes, the control unit is adapted to identify MMC activity and respond, such that false positive identifications of eating activity are reduced. For example, when a change in antral electrical activity is detected, which may be indicative of eating, control unit 32 examines data on antral electrical activity from 30 to 50 minutes prior thereto, searching for similar activity that may be indicative of MMC activity. If the current activity is likely to be related to MMC activity, then the fundic threshold level signifying an eating event is increased during the subsequent times that are between 30 and 50 minutes in the future (i.e., when subsequent MMC activity is expected), thus reducing the likelihood of false positives relating to MMC contractions. As appropriate, other periodic physiological activities of the gastrointestinal system are treated in a similar manner. It is to be understood that the period of the MMC activity is described herein as being between 30 and 50 minutes by way of illustration and not limitation. In some subjects, the period of the MMC activity may be higher, e.g., 50 to 90 minutes, or 90 to 120 minutes. For some applications, a calibration period is provided to determine the length of the period for each subject.

In an embodiment of the present invention, in order to increase satiety of the subject, control unit 32 drives electrodes 38 to apply an enhancement signal to a wall of stomach 36. The enhancement signal typically includes as appropriate, an Excitable-Tissue Control (ETC) signal and/or an excitatory signal which induces contraction of muscles of stomach 36. Aspects of ETC signal application are typically performed, mutatis mutandis, in accordance with techniques described in PCT Publications WO 99/03533 and WO 97/25098, and their corresponding U.S. Pat. Nos. 6,571,127 and 6,317,631, which are incorporated herein by reference. For some applications, the ETC signal is applied responsive to natural electrical activity of stomach 36, for example, after a designated delay following a detected activation of a portion of stomach 36. For these applications, apparatus and methods may be used, mutatis mutandis, that are described in U.S. Pat. No. 6,587,721 to Prutchi et al. and PCT Publication WO 06/018851 to Kliger et al., which are incorporated herein by reference.

In an embodiment of the present invention, control unit 32 drives electrodes 38 to apply the enhancement signal to muscle in one area of stomach 36, so as to induce a contraction of the stimulated muscle which, in turn, causes stretching and/or "pinching" (local, high-intensity contraction) of stretch-receptors in an adjacent portion of stomach 36. This form of contraction-mediated stretching simulates the normal appetite-reduction action of the stomach's stretch-receptors, without the subject having eaten the quantities of food which would normally be required to trigger this appetite-reduction response. For example, control unit 32 may generate an enhancement signal which causes contraction of the corpus of stomach 36 at the beginning of a meal, whereby a substantial amount of food will accumulate in the fundus. This accumulation, in turn, increases intra-gastric pressure and stretches the fundic walls to a greater extent than would be caused without the applied enhancement signal.

In an embodiment of the present invention, control unit 32 drives electrodes 38 to apply the enhancement signal so as to create a contraction pattern of some of the muscles of stomach 36, in order to reduce the cross-sectional area of a portion of stomach 36. This reduction is believed to increase the sensation of satiety felt by the subject compared to that which was felt prior to application of the enhancement signal. Typically, the enhancement signal is configured such that the cross-sectional area of stomach 36 is reduced by at least 20%, and this reduction is maintained in one region of the stomach for a period of at least 1 minute. It is to be understood that for some applications, greater or lesser reductions in cross-sectional area may be desirable, and these may be maintained for periods greater or less than 1 minute.

Alternatively or additionally, for some applications, the feeling of satiety is induced by applying electrical signals which enhance the mobility of chyme from fundus 60 to antrum 58 of stomach 36, where stretch-receptor signals are generally generated to a greater extent for a given quantity of food than in the fundus. Further alternatively or additionally, control unit 32 is configured to drive electrodes 38 to generate, from within stomach 36, an electrical field that stimulates a pancreas and/or one or more nearby organs of the subject, in order to increase satiety of the subject. Still further alternatively or additionally, the electrical field generated by electrodes 38 increases satiety through an indirect effect on pancreatic activity, e.g., mediated hormonally or by the nervous system. Yet further alternatively or additionally, the electrical field generated by electrodes 38 modulates the blood-sugar-controlling activity of a portion of the gastrointestinal tract, pancreas, and/or liver.

In an embodiment of the present invention, signal generation unit 54 generates ETC signals as a pulse train, immediately or within 0.1, 1, 5, or 10 seconds following detected gastric electrical activity. For some applications, the ETC signals have a pulse train frequency of between about 40 and about 120 Hz (e.g., about 83 for gastric stimulation), a pulse train duration of between about 200 and about 2500 ms (e.g., about 1200 ms), and peak-to-peak amplitudes between about +/−1 mA and about +/−20 mA (e.g., about +/−10 mA). Alternatively or additionally, for reducing blood glucose levels, parameters described in the above mentioned PCT Publication WO 05/087310 may be used.

Figure 3A:
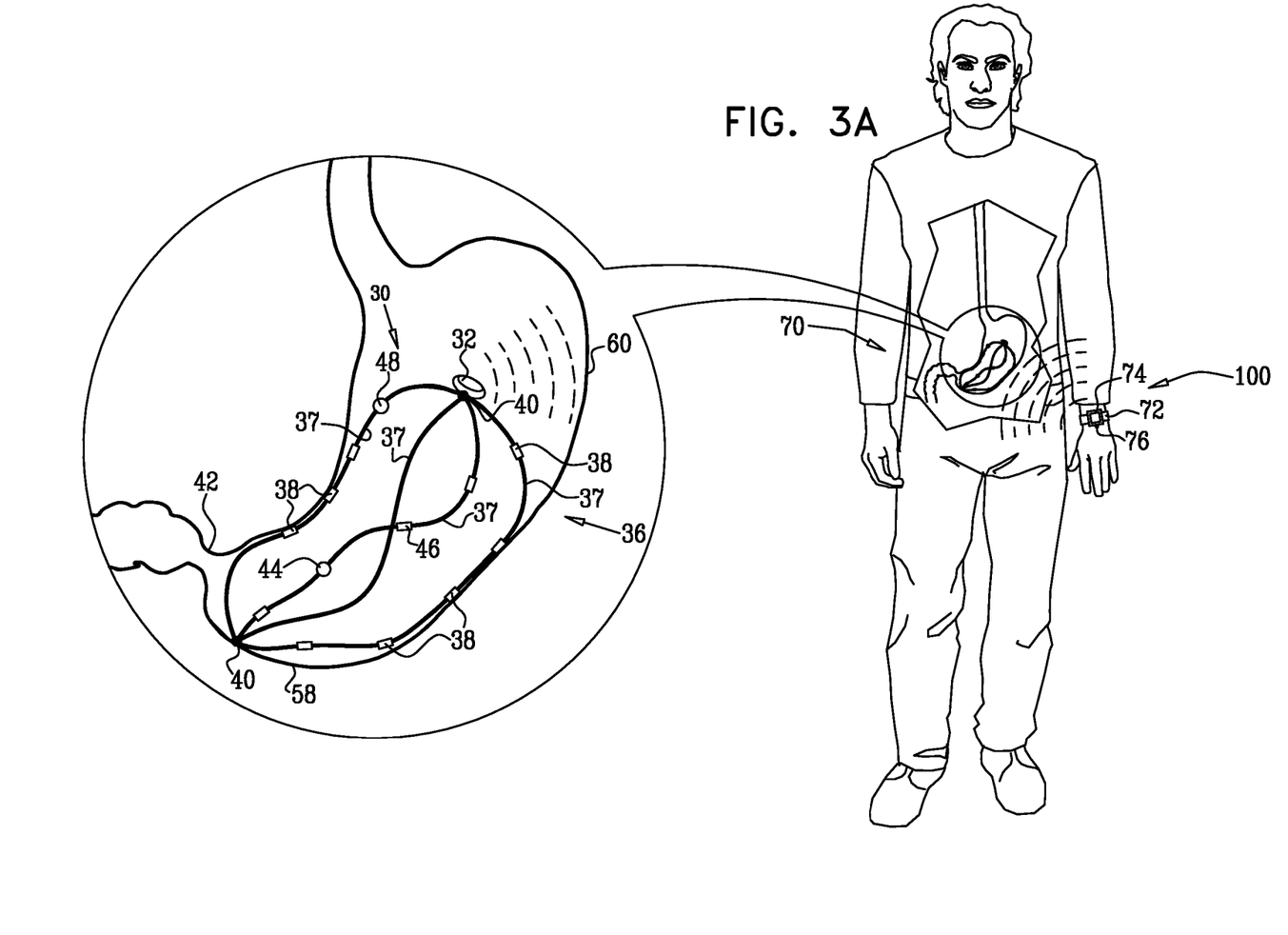
FIGS. 3A-B are schematic illustrations of an external communication device and the system of FIGS. 1A-C, in accordance with respective embodiments of the present invention.

Reference is now made to FIG. 3A, which is a schematic illustration of apparatus 70 comprising an external communication device 100 in communication with control unit 32, in accordance with an embodiment of the present invention. Control unit 32 is configured to wirelessly communicate with external communication device 100, typically using radio frequency transmission. The communication is typically bidirectional, wherein control unit 32 transmits data indicative of a state of stomach 36 to external communication device 100, and wherein external communication device 100 transmits data to control unit 32. Control unit 32, in turn, drives the electrodes to apply the electrical signal to the stomach wall.

For some applications, control unit 32 is adapted to detect a parameter in the vicinity of capsule 34 and transmit an indication of the parameter from capsule 34 to external communication device 100. Typically, the parameter represents eating by the subject, and control unit 32 detects the eating as described hereinabove with reference to FIG. 2. In response to detecting the parameter, control unit 32 transmits an indication of the parameter to external communication device 100. In response to the transmission, external communication device 100 conveys the state of stomach 36 to the subject or to a physician. Such conveying may be in real time, or according to a schedule (e.g., a daily summary of diet adherence). Alternatively or additionally, once the subject is informed, he/she programs external communication device 100 to transmit data, e.g., a stimulation protocol, to control unit 32, in response to the transmission of the sensed parameter from control unit 32. For example, if control unit 32 over-reports or under-reports incidences of the subject eating, a threshold in an eating detection algorithm may be changed.

For some applications, the communication between control unit 32 and external communication device 100 is unidirectional. External communication device 100 is configured to generate a stimulation protocol for electrode device 30, and transmit data representing the protocol from outside a body of the subject to control unit 32. Alternatively, control unit 32 transmits an indication of a state of stomach 36 to external communication device 100, to be conveyed to the subject or a physician.

In the embodiment shown in FIG. 3A, external communication device 100 comprises a watch 72 configured to be worn on the wrist of the subject. Watch 72 is configured to convert data transmitted from control unit 32 into comprehensible data to be displayed on a display 74 of watch 72, effectively conveying data representing a state of stomach 36 to the subject.

An input device 76 is configured to receive input from the subject. Using input device 76, the subject transmits a start time of eating and/or a termination time of eating to control unit 32. Alternatively, input device 76 receives an input indicating a quality of a meal (e.g., solid, liquid, fruits & vegetables, dessert), and control unit 32 adjusts a stimulation protocol in accordance therewith. Further alternatively, the subject or physician transmits an indication of a strength of the electrical signal, e.g., signal amplitude, frequency, or duty cycle, to be applied to the stomach wall. The input is then transmitted to control unit 32. In response to the input by the subject, control unit 32 drives electrode device 30 to apply a desired electrical signal to the stomach wall.

Figure 3B:
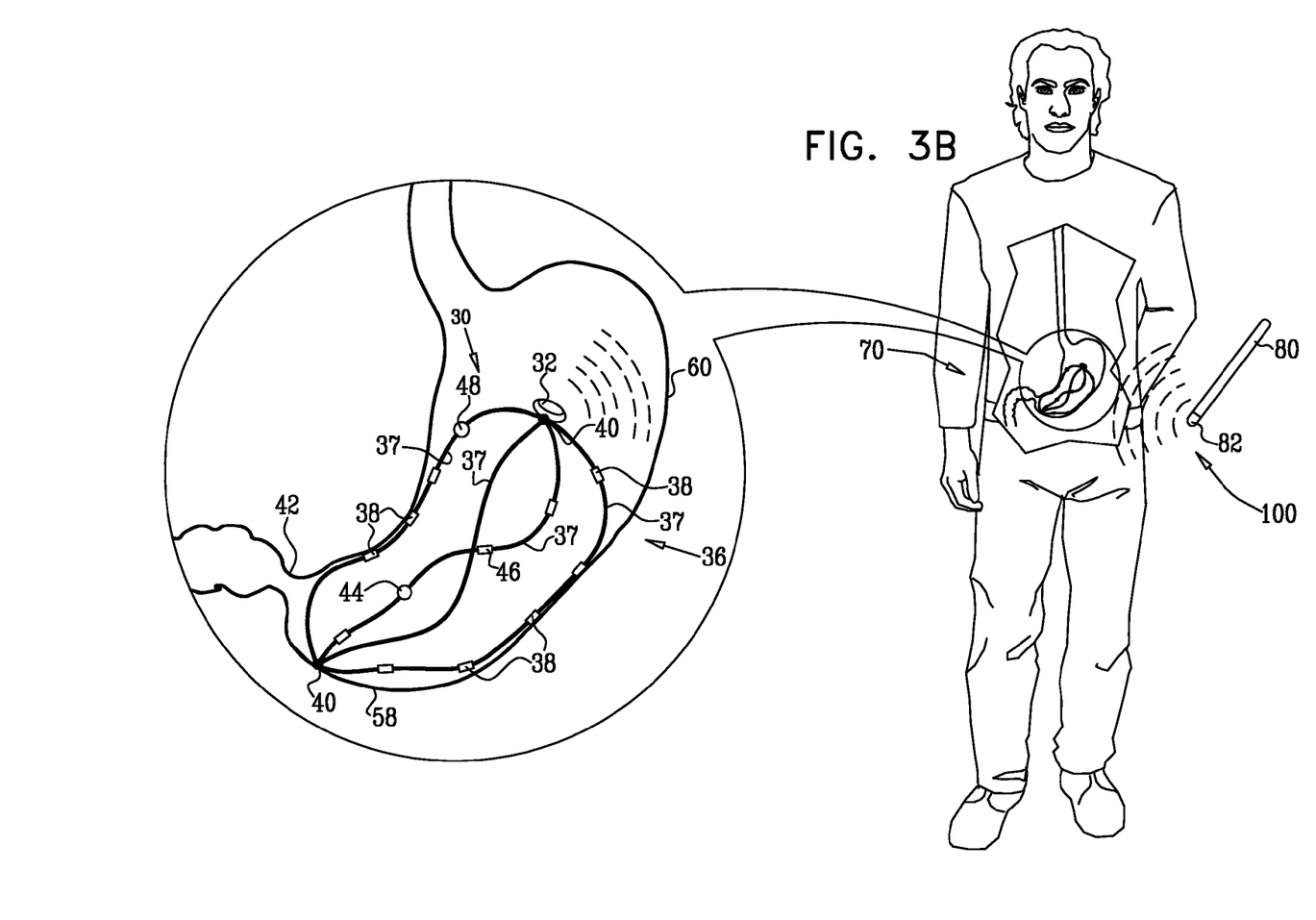

Reference is now made to FIG. 3B which is a schematic illustration of apparatus 70 as described hereinabove with reference to FIG. 3A, with the exception that external communication device 100 comprises a wand 80 and a radio frequency transmitting device 82. Wand 80 is typically used by a physician desiring to assess a response of the subject to the applied electrical signal. In response to the assessment, the physician may set a stimulation protocol for signal application by electrode device 30 of an ingestible capsule 34.

Figure 4A:
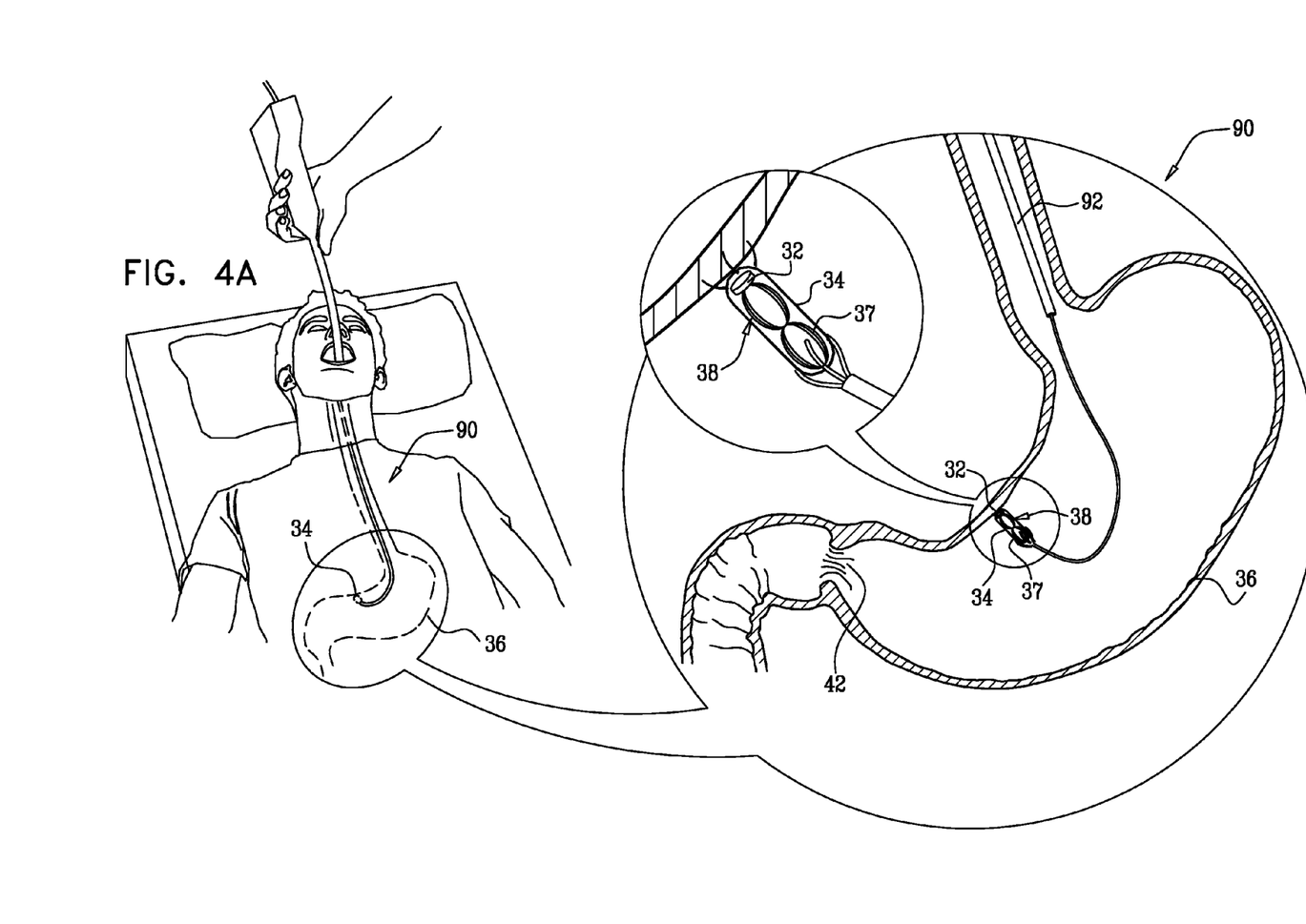
FIGS. 4A-B are schematic illustrations of an implantable food intake regulation system, in accordance with an embodiment of the present invention.

Reference is now made to FIG. 4A, which is a schematic illustration of a food intake regulation system 90 configured to be implanted in stomach 36 of the subject, in accordance with an embodiment of the present invention. Capsule 34 is guided into stomach 36 using an endoscope 92. A securing mechanism (e.g., a hook or suture), coupled to capsule 34, is configured to be endoscopically mounted to the stomach wall, thereby implanting system 90 within stomach 36.

For some applications, food intake regulation system 90 or a gastric stimulator known in the art is designated for chronic implantation, following assessment via ingestible capsule 34 of an indication that electrical signal application to stomach 36 produces weight loss in a given subject.

Figure 4B:
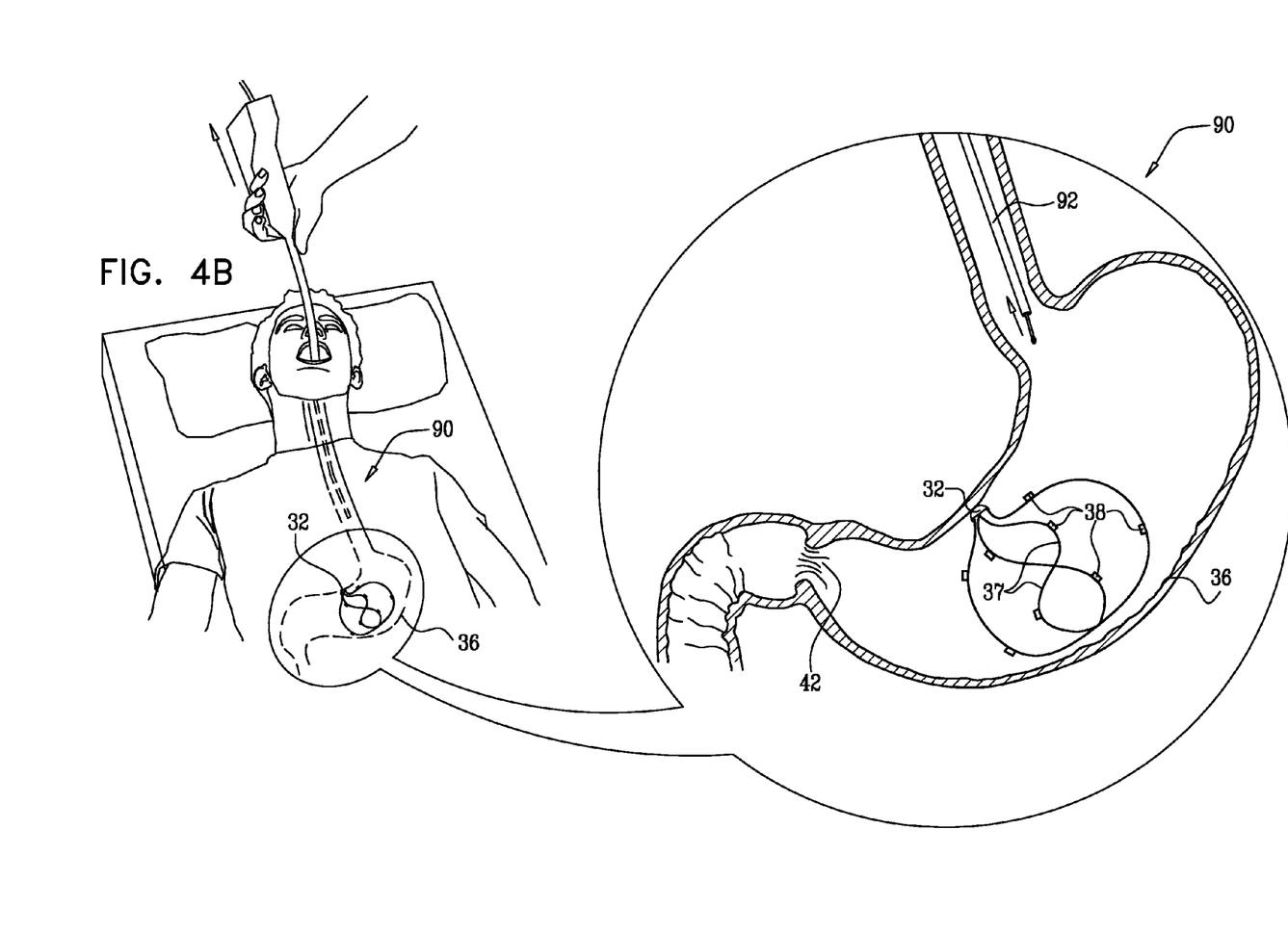

Reference is now made to FIG. 4B, which is a schematic illustration of food intake regulation system 90 as described hereinabove with reference to FIG. 4A, showing a endoscope 92 being retracted from stomach 36. Concomitant dissolving of a coating of capsule 34 occurs to allow for expansion of support elements 37 such that at least a portion of the electrodes comes in contact with the stomach wall.

It is to be understood that methods and apparatus described hereinabove may be used in combination with drug treatments or in combination with other therapies designed to treat obesity and/or diabetes, and/or facilitate greater subject control of eating habits. The scope of the present invention includes embodiments described in the following patents and patent applications, which are incorporated herein by reference. In an embodiment, techniques and apparatus described in one or more of the following patents and patent applications are combined with techniques and apparatus described herein:

U.S. Provisional Patent Application 60/602,550, filed Aug. 18, 2004, entitled, "Monitoring, analysis, and regulation of eating habits".

PCT Patent Publication WO 02/082968 to Policker et al.

U.S. patent application Ser. No. 10/250,714, which published as U.S. Patent Application Publication 2004/0059393 to Policker et al.

U.S. Pat. No. 6,600,953 to Flesler et al.;

U.S. Pat. No. 6,415,178 and PCT Patent Publication WO 98/10830 to Ben-Haim et al.

U.S. Pat. No. 6,571,127 and PCT Patent Publication WO 99/03533 to Ben-Haim et al., and/or PCT Publication WO 05/087310 to Harel et al.; and/or PCT Publication WO 05/007232 to Ben Haim et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for treating a subject, comprising:
an electrode device, which comprises:
a plurality of electrodes;
one or more flexible support elements, which are coupled to the electrodes, and are adapted to expand in a stomach of a subject, such that (a) the electrode device cannot pass from the stomach, and (b) at least a portion of the electrodes comes in contact with a wall of the stomach at least a portion of the time that the electrodes are in the stomach, wherein the support elements are adapted to remain in the stomach for at least 24 hours, and at least a portion of the electrode device is adapted to thereafter come apart to thereby allow passage of the electrode device from the stomach; and
a control unit, adapted to drive the electrodes to apply an electrical signal to the stomach wall; and
an ingestible capsule, adapted to hold the electrode device during ingestion of the capsule by the subject, and to release the electrode device in the stomach.

2. The apparatus according to claim 1, wherein the electrode device is configured to remain in the stomach for at least one week.

3. The apparatus according to claim 1, wherein the control unit is adapted to drive the electrodes to apply the electrical signal to the stomach wall responsively to eating by the subject.

4. The apparatus according to claim 1, further comprising one or more coupling elements, which couple the support elements to one another, and which are adapted to dissolve, thereby allowing the at least a portion of the electrode device to come apart.

5. The apparatus according to claim 1, wherein the support elements comprise a material adapted to dissolve, thereby allowing the at least a portion of the electrode device to come apart.

6. The apparatus according to claim 1, wherein the control unit is adapted to drive the electrodes to apply an Excitable-Tissue Control (ETC) signal to the stomach wall.

7. The apparatus according to claim 1, wherein the ingestible capsule comprises a material configured to dissolve in the stomach.

8. The apparatus according to claim 1, wherein the support elements comprise electrically conductive sections which are configured to function as the electrodes.

9. The apparatus according to claim 1, wherein the plurality of electrodes comprise one or more local sense electrodes.

10. The apparatus according to claim 1, comprising at least one physiological sensor, wherein the control unit is configured to drive the electrodes in response to a signal from the physiological sensor.

11. The apparatus according to claim 1, wherein the control unit is adapted to configure the electrical signal to increase satiety of the subject.

12. The apparatus according to claim 1, wherein the control unit is adapted to configure the signal to modulate a parameter of a contraction generated by stomach muscle of the subject.

13. The apparatus according to claim 1, wherein the electrode device is configured to be too large, while expanded, to pass through a pylorus of the subject.

14. Apparatus for treating a subject, comprising:
a plurality of electrodes;
one or more flexible support elements, which are coupled to the electrodes, and are adapted to expand in a stomach of a subject, such that at least a portion of the electrodes comes in contact with a wall of the stomach at least a portion of the time that the electrodes are in the stomach, the support elements adapted to remain in the stomach for at least 24 hours;
a control unit, adapted to drive the electrodes to apply an electrical signal to the stomach wall and to configure the signal to modulate a blood glucose level of the subject by stimulating a non-gastric organ; and
an ingestible capsule, adapted to hold the support elements, electrodes, and control unit during ingestion of the capsule by the subject, and to release the support elements, electrodes, and control unit in the stomach.

15. The apparatus according to claim 14, wherein the non-gastric organ is a pancreas of the subject, and wherein the control unit is adapted to configure the signal to modulate the blood glucose level by generating an electrical field within the stomach that directly stimulates the pancreas.

16. The apparatus according to claim 14, wherein the control unit is adapted to drive the electrodes to apply an Excitable-Tissue Control (ETC) signal to the stomach wall.

17. The apparatus according to claim 14, wherein the ingestible capsule comprises a material configured to dissolve in the stomach.

18. The apparatus according to claim 14, wherein the support elements comprise electrically conductive sections which are configured to function as electrodes.

19. The apparatus according to claim 14, wherein the plurality of electrodes comprise one or more local sense electrodes.

20. The apparatus according to claim 14, comprising at least one physiological sensor, wherein the control unit is configured to drive the electrodes in response to a signal from the physiological sensor.

21. The apparatus according to claim 14, wherein the control unit is adapted to configure the electrical signal to increase satiety of the subject.

22. The apparatus according to claim 14, wherein the control unit is adapted to drive the electrodes to apply the electrical signal to the stomach wall responsively to eating by the subject.

23. The apparatus according to claim 14, wherein the control unit is adapted to configure the signal to modulate a blood-hormone level associated with pancreatic activity.

24. The apparatus according to claim 14, wherein the control unit is adapted to configure the signal to modulate a parameter of a contraction generated by stomach muscle of the subject.

25. The apparatus according to claim 14, wherein the control unit is adapted to configure the electrical signal to reduce a blood glucose level of the subject.

26. The apparatus according to claim 14, wherein the control unit is adapted to detect eating by the subject by monitoring electrical changes in the stomach, and to drive the electrodes to apply the electrical signal to the stomach wall responsively to detecting the eating by the subject.

* * * * *